(12) United States Patent
Webster et al.

(10) Patent No.: US 6,210,444 B1
(45) Date of Patent: Apr. 3, 2001

(54) TIBIAL KNEE COMPONENT WITH A MOBILE BEARING

(75) Inventors: Vincent A. Webster, Warsaw; Clayton R. Miller, Bremen, both of IN (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/421,869

(22) Filed: Oct. 26, 1999

(51) Int. Cl.$^7$ ........................................................ A61F 2/38
(52) U.S. Cl. .................................. 623/20.33; 623/20.24; 623/20.14
(58) Field of Search ................................ 623/20.14, 20.21, 623/20.23, 20.24, 20.32, 20.33, 20.34

(56) References Cited

U.S. PATENT DOCUMENTS

| | | |
|---|---|---|
| 4,085,466 | 4/1978 | Goodfellow et al. . |
| 4,094,017 | 6/1978 | Matthews et al. . |
| 4,136,405 | 1/1979 | Pastrick et al. . |
| 4,216,549 | 8/1980 | Hillberry et al. . |
| 4,219,893 | 9/1980 | Noiles . |

(List continued on next page.)

FOREIGN PATENT DOCUMENTS

| | | | |
|---|---|---|---|
| 0 472 475 A2 | 7/1991 | (EP) | ................................ A61F/2/38 |
| 0 498 586 A1 | 1/1992 | (EP) | ................................ A61F/2/38 |
| 0 519 872 A1 | 6/1992 | (EP) | ................................ A61F/2/38 |
| 0 592 750 B1 | 12/1992 | (EP) | ................................ A61F/2/38 |
| 0 670 151 A2 | 1/1995 | (EP) | ................................ A61F/2/38 |
| 0 636 353 A1 | 2/1995 | (EP) | ................................ A61F/2/38 |
| 0 674 887 A1 | 3/1995 | (EP) | ................................ A61F/2/38 |
| 79 20563 | 8/1979 | (FR) | ................................ A61F/1/00 |
| 2 277 034 | 10/1994 | (GB) | ................................ A61F/2/38 |
| 2 278 782 | 12/1994 | (GB) | ................................ A61F/2/38 |
| 2 280 375 | 2/1995 | (GB) | ................................ A61F/2/38 |
| 2 291 355 | 7/1995 | (GB) | ................................ A61F/2/38 |
| 2 291 355 | 1/1996 | (GB) | ................................ A61F/2/38 |
| 2 293 109 | 3/1996 | (GB) | ................................ A61F/2/38 |
| 2 304 051 | 3/1997 | (GB) | ................................ A61F/2/38 |
| 2 312 166 | 10/1997 | (GB) | ................................ A61F/2/38 |
| 2 312 167 | 10/1997 | (GB) | ................................ A61F/2/38 |
| 2 312 168 | 10/1997 | (GB) | ................................ A61F/2/38 |

(List continued on next page.)

OTHER PUBLICATIONS

The Mechanical Testing of a Sliding Meniscus Knee Prosthesis; R. J. Minns, B.Eng., M.Sc., Ph.D., J. Campbell, CH.B., M.Ch. (Ortho), FRCS, Clinical Orthopaedics; Nov.–Dec. 1978, vol. 137, pp. 268–275.

(List continued on next page.)

Primary Examiner—Gene Mancene
Assistant Examiner—Michael B. Priddy
(74) Attorney, Agent, or Firm—Todd A. Dawson

(57) ABSTRACT

An orthopaedic knee component for implanting within a proximal tibia includes a tibial tray with a proximal tibial plateau and a distally extending stem. The tibial tray also includes a recess extending into the tibial plateau. The recess is configured to define a first rotational stop and a second rotational stop. The tibial tray further includes a generally cylindrical post positioned within the recess. The post extends generally orthogonal to the tibial plateau and defines an axis of rotation. A bearing is carried by the tibial tray and has an articular bearing surface for engagement with a femoral component. The bearing has an opening in which the post is disposed. The opening and the post allow pivotal movement of the bearing relative to the tibial plateau about the axis of rotation. The bearing further has a projection extending into the recess of the tibial tray. The projection is configured to abut the first rotational stop when the bearing is at a first rotational limit and is configured to abut the second rotational stop when the bearing is at a second rotational limit.

7 Claims, 3 Drawing Sheets

U.S. PATENT DOCUMENTS

| | | |
|---|---|---|
| 4,224,696 | 9/1980 | Murray et al. . |
| 4,224,697 | 9/1980 | Murray et al. . |
| 4,257,129 | 3/1981 | Volz . |
| 4,262,368 | 4/1981 | Lacey . |
| 4,301,553 | 11/1981 | Noiles . |
| 4,309,778 | 1/1982 | Buechel et al. . |
| 4,470,158 | 9/1984 | Pappas et al. . |
| 4,586,933 | 5/1986 | Shoji et al. ............... 623/20 |
| 4,634,444 | 1/1987 | Noiles ...................... 623/20 |
| 4,728,332 | 3/1988 | Albrektsson ............. 623/20 |
| 4,888,021 | 12/1989 | Forte et al. .............. 623/20 |
| 4,950,297 | 8/1990 | Elloy et al. .............. 623/20 |
| 5,011,496 | 4/1991 | Forte et al. .............. 623/20 |
| 5,080,675 | 1/1992 | Lawes et al. ............ 623/20 |
| 5,171,283 | 12/1992 | Pappas et al. ........... 623/20 |
| 5,271,737 | * 12/1993 | Baldwin et al. ......... 623/20 |
| 5,271,747 | 12/1993 | Wagner et al. .......... 623/20 |
| 5,282,868 | 2/1994 | Bahler ...................... 623/20 |
| 5,314,481 | 5/1994 | Bianco ..................... 623/20 |
| 5,314,483 | 5/1994 | Wehrli et al. ............ 623/20 |
| 5,330,533 | 7/1994 | Walker ..................... 623/20 |
| 5,344,460 | 9/1994 | Turanyi et al. .......... 623/20 |
| 5,358,527 | 10/1994 | Forte ........................ 623/20 |
| 5,358,530 | 10/1994 | Hodorek .................. 623/20 |
| 5,358,531 | 10/1994 | Goodfellow et al. ... 623/20 |
| 5,370,701 | 12/1994 | Finn ......................... 623/20 |
| 5,387,240 | 2/1995 | Pottenger et al. ....... 623/20 |
| 5,395,401 | 3/1995 | Bahler ...................... 623/20 |
| 5,413,604 | 5/1995 | Hodge ...................... 623/20 |
| 5,413,608 | 5/1995 | Keller ....................... 623/20 |
| 5,458,644 | 10/1995 | Grundei ................... 623/20 |
| 5,480,446 | 1/1996 | Goodfellow et al. ... 623/20 |
| 5,549,689 | 8/1996 | Epstein et al. ........... 623/20 |
| 5,556,432 | 9/1996 | Kubein-Meesenburg et al. .... 623/20 |
| 5,609,639 | 3/1997 | Walker ..................... 623/20 |
| 5,609,644 | 3/1997 | Ashby et al. ............ 623/20 |
| 5,658,342 | 8/1997 | Draganich et al. ...... 623/20 |
| 5,683,468 | 11/1997 | Pappas ..................... 623/20 |
| 5,702,466 | 12/1997 | Pappas et al. ........... 623/20 |
| 5,725,584 | 3/1998 | Walker et al. ........... 623/20 |
| 5,755,804 | * 5/1998 | Schmotzer et al. ..... 623/20 |
| 5,879,394 | 3/1999 | Ashby et al. ............ 623/20 |
| 5,951,603 | * 9/1999 | O'Neil et al. ............ 623/20 |
| 5,954,770 | * 9/1999 | Schmotzer et al. ..... 623/20 |
| 6,090,144 | * 7/2000 | Letot et al. .............. 623/20 |

FOREIGN PATENT DOCUMENTS

| | | | |
|---|---|---|---|
| 2 312 377 | 10/1997 | (GB) | ................. A61F/2/38 |
| 2 313 314 | 11/1997 | (GB) | ................. A61F/2/38 |
| WO 95/22303 | 8/1995 | (WO) | ................. A61F/2/38 |
| WO 95/25484 | 9/1995 | (WO) | ................. A61F/2/38 |
| WO 95/27450 | 10/1995 | (WO) | ................. A61F/2/38 |
| WO 95/30390 | 11/1995 | (WO) | ................. A61F/2/38 |
| WO 96/01087 | 1/1996 | (WO) | ................. A61F/2/38 |
| WO 96/03097 | 2/1996 | (WO) | ................. A61F/2/38 |

OTHER PUBLICATIONS

S–ROM® Modular Total Knee System; Joint Medical Products Corp; 1993.

TRA™ Knee System Design Rationale; Nov. 1996, pp. 1–23.

New Jersey LCS® Total Knee System; DePuy; 1994.

SAL Self–Aligning Total Knee Replacement; Protek.

Difficulties With Bearing Dislocation and Breakage Using a Movable Bearing Total Knee Replacement System; James K. Weaver, M.D., Robert S. Kerkash, M.D., A. Seth Greenwald D. Phil. (Oxon); Clincal Orthopaedics and Related Research. No. 290: pp 244–252: 1993 J. B. Lippincott Company.

The Sliding Meniscus Knee Prosthesis: Design Concepts; R. J. Minns, J. Campbell.

The Design and BioMechanics of a Sliding Menisucs Knee Prosthesis; R. J. Minns; pp 306–309.

The Oxford Meniscal Knee Phase II; Biomet Ltd.; British JBJS, May 1988.

New Jersey Tricompartmental Total Knee System with Porocoat Surgical Procedure; Frederick F. Buechel, M.D.; DePuy.

New Jersey LCS™Total Knee System with Porocoat; DePuy; JBJS vol. 67–A, No. 8; Oct. 1985.

AGC Total Knee System; Biomet Ltd., British JBJS; No. 1985.

Minns Meniscal Knee—A Total Prosthesis for Early Joint Degeneration; Zimmer (Swindon).

Gliding Meniscal Knee—A Major Development in Cruciate–Retaining Arthroplasty; Zimmer (Swindon).

Longer Implant Life in Three Easy Lessons; JBJS—Jul. 1998; DePuy.

SAL Self–Aligning, An Evolution in Motion; Protek; JBJS Oct. 1997.

In 1977, The LCS™ Changed the Way Knees Work; Brit JBJS, Mach 1997; DePuy.

Study the Facts—The Oxford™ Knee; British JBJS Mar. 1998; Biomet Ltd.

Longer implant Life in Three Easy Lessons;JBJS— Jul. 1998; DePuy.

* cited by examiner

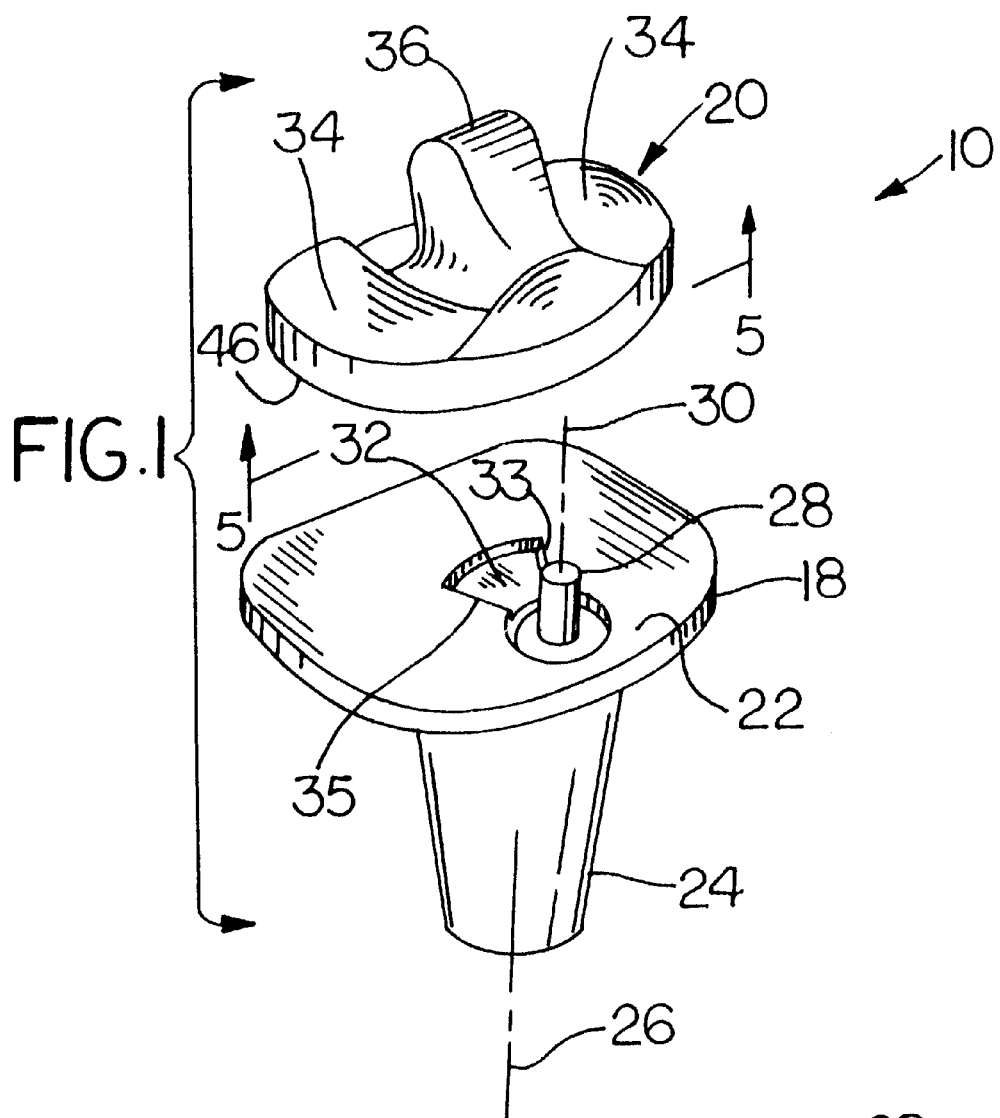
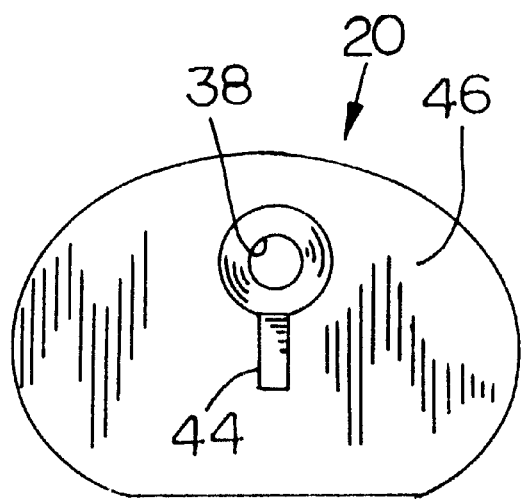

TIBIAL KNEE COMPONENT WITH A MOBILE BEARING

BACKGROUND OF THE INVENTION

1. Field of the Invention

The present invention relates to an orthopaedic implant, and, more particularly, to a tibial knee component.

2. Description of the Related Art

A tibial knee component is implanted within a proximal tibia and engages with a femoral component implanted within a distal femur. The tibial knee component typically includes a bearing which is immovably affixed to a tibial tray. The tibial tray includes a stem which is implanted within the intramedullary (IM) canal in the proximal tibia. The bearing may be in the form of a wear resistant and low friction material such as ultra high molecular weight polyethylene (UHMWPE) which is immovably attached to the tibial tray. Pivotal movement between the femoral component and the bearing surface of the bearing occurs with relatively low friction and low wear characteristics.

It is also known to provide a mobile bearing which moves relative to the tibial tray. During deep flexion between the femur and tibia, the bearing rotates about a longitudinal axis associated with a pivot point at the attachment location between the bearing and tibial tray. While some designs allow for 360 degrees of rotation between the mobile bearing and the tibial tray, most designs have a rotational limit provided. Although known designs are adequate to allow limited rotation between the bearing and tibial tray, they may be relatively complex and thus expensive to manufacture.

What is needed in the art is a tibial knee component with a mobile bearing which is easier to manufacture and still allows adequate movement between the bearing and tibial tray during deep flexion of the knee joint.

SUMMARY OF THE INVENTION

The present invention provides a tibial knee component with a tibial tray having a post and keyhole shaped recess, and a bearing having a projection positioned within the recess and an opening receiving the post.

The invention comprises, in one form thereof, an orthopaedic knee component for implanting within a proximal tibia. A tibial tray includes a proximal tibial plateau and a distally extending stem. The tibial tray also includes a recess extending into the tibial plateau. The recess is configured to define a first rotational stop and a second rotational stop. The tibial tray further includes a generally cylindrical post positioned within the recess. The post extends generally orthogonal to the tibial plateau and defines an axis of rotation. A bearing is carried by the tibial tray and has an articular bearing surface for engagement with a femoral component. The bearing has an opening in which the post is disposed. The opening and the post allow pivotal movement of the bearing relative to the tibial plateau about the axis of rotation. The bearing further has a projection extending into the recess of the tibial tray. The projection is configured to abut the first rotational stop when the bearing is at a first rotational limit and is configured to abut the second rotational stop when the bearing is at a second rotational limit.

An advantage of the present invention is that the keyhole shaped recess and projection allow rotation of the bearing between first and second rotational limits.

Another advantage is that the post and opening allow rotational movement of the bearing while not allowing radial movement of the bearing relative to the axis of rotation.

Yet another advantage is that substantially all of the bearing backing is supported by the tibial plateau at any pivotal position.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is an exploded, perspective view of an embodiment of an orthopaedic knee component of the present invention;

FIG. 5 is a bottom view of the bearing of FIGS. 1–4; and

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 6:
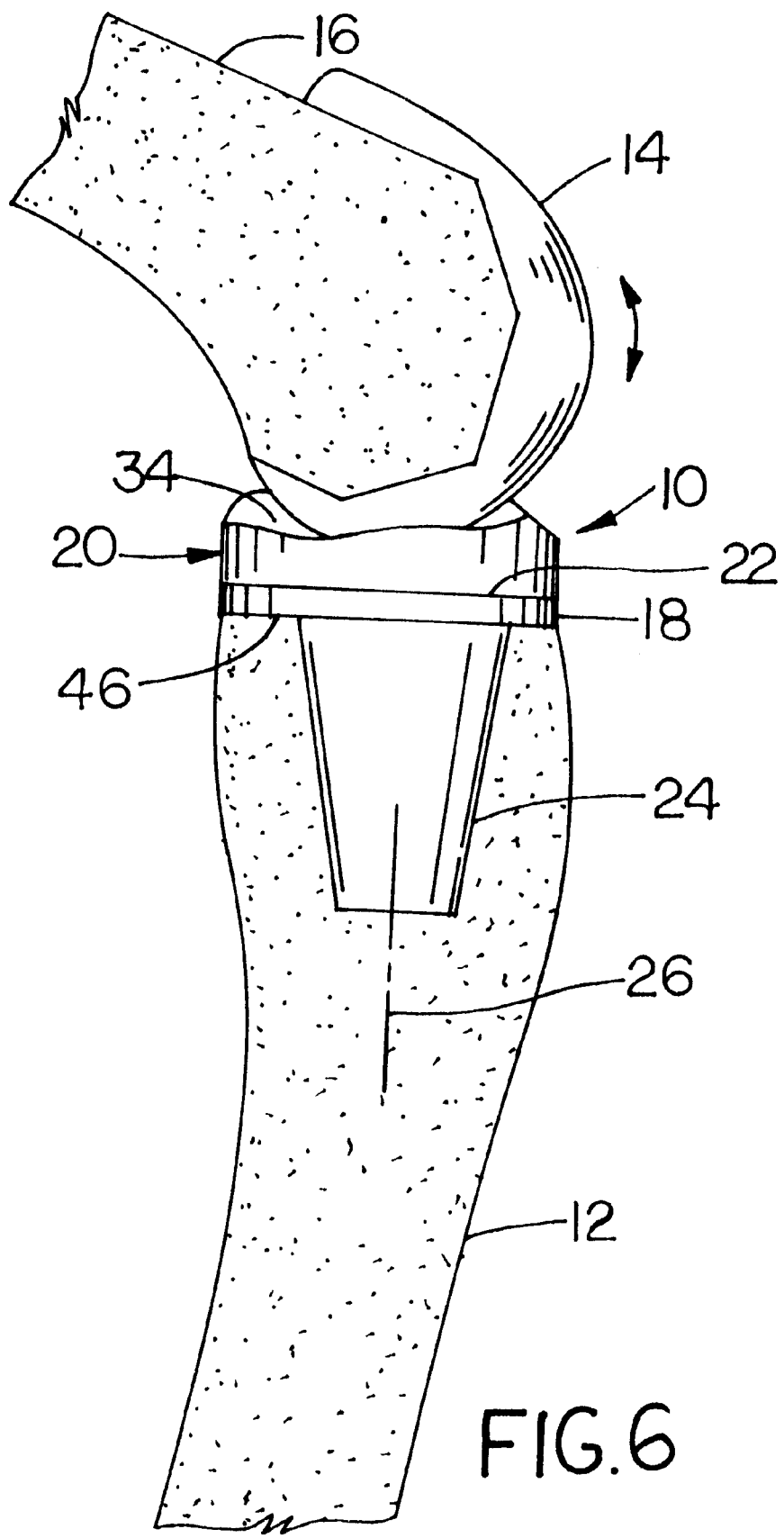
FIG. 6 is a side view of the orthopaedic knee component of FIGS. 1–4, implanted within a tibia and engaged with a femoral component.

Referring now to the drawings, and more particularly to FIGS. 1–5, there is shown an embodiment of an orthopaedic knee component in the form of a tibial knee component 10 which is implanted within a proximal tibia 12 (FIG. 6). Tibial knee component 10 engages with a femoral knee component 14 which is implanted within a distal femur 16.

Tibial knee component 10 includes a tibial tray 18 and a bearing 20. Tibial tray 18 has a proximal tibial plateau 22 and a distally extending stem 24. Tibial plateau 22 has a generally planar proximal surface which extends transverse (e.g., orthogonal) to a longitudinal axis 26 of stem 24. A generally cylindrical shaped post 28 has an axis of rotation 30 which extends generally orthogonal to tibial plateau 22, and thus also extends generally parallel to axis 26 of stem 24.

Tibial tray 18 also includes a key-hole shaped recess 32 which extends into tibial plateau 22. Recess 32 has a first wall 33 providing a first rotational stop when tibial tray is engaged with bearing 20, and a second wall 35 providing a second rotation stop when tibial tray is engaged with bearing 20, as will be described in more detail hereinafter. Recess 32 may have any suitable configuration. Post 28 is positioned within and extends from recess 32 to define axis of rotation 30.

Bearing 20 has an articular bearing surface 34 for engagement with femoral component 14. Articular bearing surface 34 is disposed on either side of a center projection 36. Each discrete portion of articular bearing surface 34 on either side of projection 36 engages a corresponding condyle of femoral knee component 14, with projection 36 being disposed between the condyles.

Bearing 20 also includes a generally cylindrical shaped opening 38 in which post 28 is disposed. Opening 38 and post 28 allow pivotal movement of bearing 20 relative to tibial plateau 22 about axis of rotation 30 of post 28. Opening 38 has a diameter which is just slightly larger than an outside diameter of post 28, such that movement of bearing 20 in a generally radial direction relative to axis 30 is inhibited.

Figure 4:
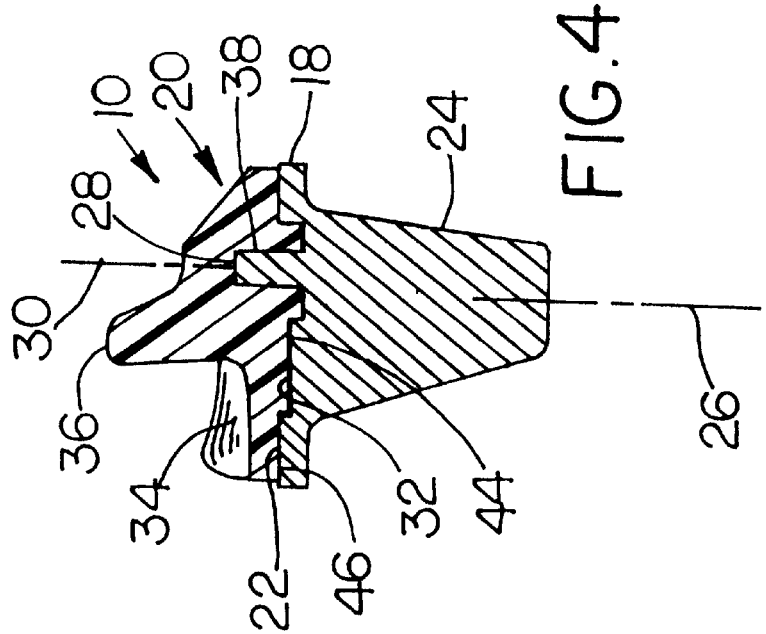
FIG. 4 is a side, sectional view of the orthopaedic knee component of FIGS. 1–3.
Figure 3:
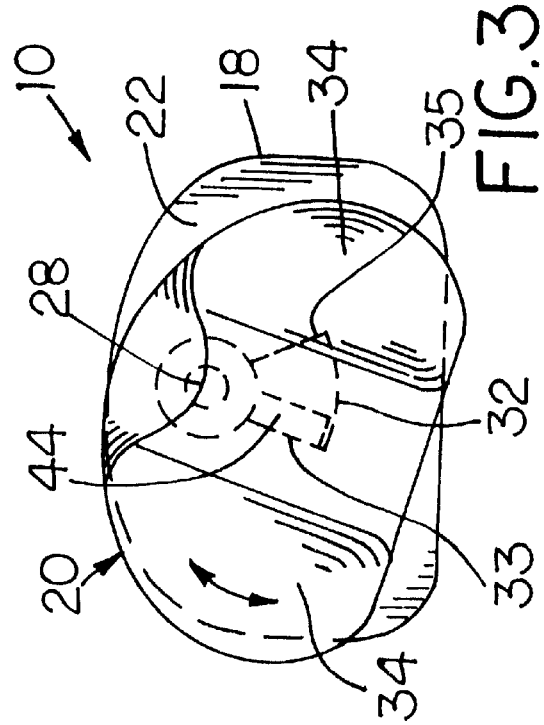
FIG. 3 is a top view of the orthopaedic knee component of FIG. 1, with the bearing in a rotated position.

Bearing 20 also includes an projection 44 extending into recess 32. Projection 44 and recess 32 allow pivotal movement of bearing 20 between a first rotational limit and a second rotational limit about axis of rotation 30. In the embodiment shown, projection 44 has a generally rectangular shape when viewed in a direction parallel to axis of rotation 30. However, projection 44 may have any suitable configuration allowing movement of bearing 20 relative to articular bearing surface 34 (e.g., pin shaped, etc.). Bearing 20 is shown in FIG. 3 at a first rotational limit which is approximately 25° relative to a neutral or symmetric position shown in FIG. 2. Thus, bearing 20 is pivotally movable through an angle of approximately 50° between the first rotational limit and the second rotational limit (in a direction opposite to that shown in FIG. 3).

Figure 2:
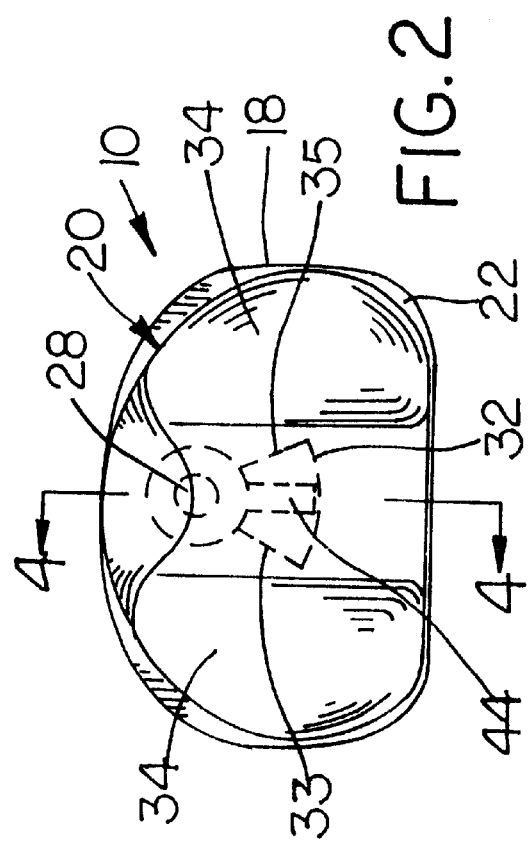
FIG. 2 is a top view of the orthopaedic knee component of FIG. 1, with the bearing in a neutral position.

Bearing 20 has a backing 46 which engages with tibial plateau 22. Backing 46 is generally planar to match the corresponding generally planar configuration of tibial plateau 22. Backing 46 defines a load bearing surface with tibial plateau which transfers the load imparted either by tibial plateau 22 or the femoral condyles engaging articular bearing surface 34. Backing 46 is sized and configured such that backing 46 is substantially entirely supported by tibial plateau 22 at any position during pivotal movement between the first rotational limit and the second rotational limit. As illustrated in FIG. 2, backing 46 of bearing 20 is entirely supported by tibial plateau 22 when bearing 20 is at a neutral position. Similarly, backing 46 is substantially entirely supported by tibial plateau 22 when bearing 20 is at a first rotational limit (FIG. 3), a second rotational limit, or any position therebetween.

With a conventional tibial knee component, the tibial tray includes a notch on the posterior side such that the tibial plateau has a generally U-shape when viewed in a proximal-distal direction. Moreover, the bearing may overhang the tibial tray by a substantial amount when the bearing is at a rotational limit. On the other hand, tibial plateau 22 of the present invention does not include a notch on the posterior side and the bearing does not overhang the tibial plateau by any appreciable amount when at a first rotational limit or a second rotational limit. Thus, bearing 20 is better supported and wear between backing 46 and tibial plateau 22 is reduced.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic knee component for implanting within a proximal tibia, comprising: a tibial tray including a proximal tibial plateau and a distally extending stem, said tibial tray also including a recess extending into said tibial plateau, said recess configured to define a first rotational stop and a second rotational stop, said tibial tray further including a generally cylindrical post positioned within said recess, said post extending generally orthogonal to said tibial plateau and defining an axis of rotation; and a bearing carried by said tibial tray and having an articular bearing surface for engagement with a femoral component, said bearing having an opening in which said post is disposed, said opening and said post allowing pivotal movement of said bearing relative to said tibial plateau about said axis of rotation, said bearing further having a projection extending into said recess of said tibial tray, said projection configured to abut said first rotational stop when said bearing is at a first rotational limit and configured to abut said second rotational stop when said bearing is at a second rotational limit.

2. The orthopaedic knee component of claim 1, wherein said recess is key-hole shaped.

3. The orthopaedic knee component of claim 1, wherein said projection is rectangular shaped when viewed in a direction parallel to said axis of rotation.

4. The orthopaedic knee component of claim 1, wherein said bearing is pivotally movable through an angle of approximately 50° between said first rotational limit and said second rotational limit.

5. The orthopaedic knee component of claim 1, wherein each of said post and said opening are generally cylindrical shaped.

6. The orthopaedic knee component of claim 5, wherein said opening in said bearing is sized to substantially inhibit movement of said bearing relative to said tibial plateau in a generally radial direction relative to said axis of rotation.

7. The orthopaedic knee component of claim 6, wherein said opening includes a first diameter corresponding to a diameter of said post.

* * * * *